(12) United States Patent
Bellinati et al.

(10) Patent No.: US 11,857,558 B2
(45) Date of Patent: Jan. 2, 2024

(54) DENTAL AND MEDICAL COMPOSITIONS HAVING A MULTIPLE SOURCE OF METALLIC IONS

(71) Applicant: ANGELUS INDÚSTRIA DE PRODUTOS ODONTOLÓGICOS S/A, Londrina-Paraná (BR)

(72) Inventors: César Eduardo Bellinati, Londrina-Paraná (BR); Cristiane Vila, Londrina-Paraná (BR); William Pereira Dos Santos, Londrina-Paraná (BR); Maíra Bendlin Calzavara, Londrina-Paraná (BR)

(73) Assignee: ANGELUS INDÚSTRIA DE PRODUTOS ODONTOLÓGICOS S/A, Londrina-Paraná (BR)

( * ) Notice: Subject to any disclaimer, the term of this patent is extended or adjusted under 35 U.S.C. 154(b) by 684 days.

(21) Appl. No.: 16/568,834

(22) Filed: Sep. 12, 2019

(65) Prior Publication Data

US 2020/0085847 A1 Mar. 19, 2020

Related U.S. Application Data

(60) Provisional application No. 62/766,612, filed on Sep. 14, 2018.

(51) Int. Cl.
| | | |
|---|---|---|
| *A61K 31/695* | (2006.01) | |
| *A61K 6/76* | (2020.01) | |
| *C08F 30/08* | (2006.01) | |

(52) U.S. Cl.
CPC .............. *A61K 31/695* (2013.01); *A61K 6/76* (2020.01); *C08F 30/08* (2013.01); *A61K 2800/412* (2013.01); *A61K 2800/623* (2013.01)

(58) Field of Classification Search
CPC ................................ A61K 31/695; A61K 6/76
See application file for complete search history.

(56) References Cited

U.S. PATENT DOCUMENTS

| | | | |
|---|---|---|---|
| 3,978,205 A | 8/1976 | Newman et al. | |
| 4,986,981 A * | 1/1991 | Glace ...................... | A61K 8/26 424/57 |
| 5,286,478 A | 2/1994 | Persello | |
| 8,475,811 B2 | 7/2013 | Yang et al. | |
| 8,765,163 B2 | 7/2014 | Zreiqat et al. | |
| 2010/0324677 A1 * | 12/2010 | Zreiqat .................... | C04B 35/22 427/2.24 |
| 2012/0027696 A1 * | 2/2012 | Pilch ........................ | A61K 8/19 424/49 |
| 2015/0183687 A1 | 7/2015 | Engqvist et al. | |
| 2017/0128329 A1 * | 5/2017 | Vemishetti .............. | A61K 8/731 |

FOREIGN PATENT DOCUMENTS

| | | |
|---|---|---|
| EP | 2695850 A1 | 2/2014 |
| WO | 2004093734 A3 | 11/2004 |
| WO | 2009052583 A1 | 4/2009 |
| WO | WO-2011098438 A1 * 8/2011 | ......... A61L 24/0015 |

OTHER PUBLICATIONS

Chen et al., "Silicate bioceramic/PMMA composite bone cement with distinctive physicochemical and bioactive properties", 2015, RSC Advances, vol. 5, pp. 37314-37322. (Year: 2015).*
Baino et al., "Bioactive Glasses: Where Are We and Where Are We Going?" J. Funct. Biomat. 9, 25; doi: 10.3390/fb9010025, 2018.
Baratieri et al., "Effect of Pulp Protection Technique on the Clinical Performance of Amalgam Restorations: Three-Year Results," Operative Dentistry 27, 319-24, 2002.
Corralo & Maltz, "Clinical and Ultrastructural Effects of Different Liners/Restorative Materials on Deep Carious Dentin: A Randomized Clinical Trial," Caries Res. 47, 243-50, 2013.
Dorozhkin, "Calcium Orthophosphates as Bioceramics: State of the Art," J. Funct. Biomater. 1, 22-107, 2010.
Fiume et al., "Bioactive Glasses: From Parent 4585 Composition to Scaffold-Assisted tissue-Healing therapies," J. Functional Biomaterials, 9, 24; doi: 10.3390/jfb9010024, 2018.
Hench & Jones,"Bioactive Glasses: Frontiers and Challenges," Frontiers in Bioengineering and Biotechnology 3, Article 194, 2015.
Hench et al., "Bonding Mechanisms at the Interface of Ceramic Prosthetic Materials," J. Biomed. Mater. Res. Symposium 2(1), pp. 117/141, 1971.
Heness & Ben-Nissan, "Innovative Bioceramics," Materials Forum 27, 104-14, 2004.
Hoppe et al., "A review of the biological response to ionic dissolution products from bioactive glasses and glass-ceramics," Biomaterials 32, 2757-74, 2011.
Iwata et al., "Sintering behavior and apatite formation of diopside prepared by coprecipitation process," Colloids and Surfaces B: Biointerfaces 24, 239-45, 2004.
Kharaziha & Fathi, "Synthesis and characterization of bioactive forsterite nanopowder," Ceramics International 35, 2449-54, 2009.
Marchi et al., "Indirect Pulp Capping in the Primary Dentition: a 4 Year Follow-up Study," J. Pediatric Dentistry 31, p. 68-71, 2006.
Mohammadi et al., "Bioinorganics in Bioactive Calcium Silicate Ceramics for Bone Tissue Repair: Bioactivity and Biological Properties," J. Ceramic Science and Technology 5, 1-12, 2014.

(Continued)

*Primary Examiner* — Michael B. Pallay
(74) *Attorney, Agent, or Firm* — Banner & Witcoff, Ltd.

(57) ABSTRACT

This disclosure provides bioceramic compositions of multiparticulate crystalline multimetallic silicates having silica double tetrahedra structures, such as Strontium-akermanite ($Sr_2MgSi_2O_7$), Akermanite ($Ca_2MgSi_2O_7$), Baghdadite ($Ca_3ZrSi_2O_9$), Hardystonite ($Ca_2ZnSi_2O_7$), as sources for controlled release of multiple metallic ions, such as $Ca^{2+}$, $Mg^{2+}$, $Zr^{4+}$, $Sr^{2+}$, $Zn^{2+}$ for medical and dental use. This disclosure also includes medical and dental uses of the disclosed compositions, for example, in tissue regeneration, including bone tissue.

13 Claims, 10 Drawing Sheets

(56) References Cited

OTHER PUBLICATIONS

Sadaghiani et al., "Growth Factor Liberation and DPSC Response Following Dentine Conditioning," J. Dental Research 1-10, 2016.
U.S. Appl. No. 16/131,268 non-final Office Action dated Mar. 1, 2019.
Smith et al., "Exploiting the Bioactive Properties of the Dentin-Pulp Complex in Regenerative Endodontics," JOE 42 (1), 2016.
Wu & Chang, "A review of bioactive silicate ceramics," Biomed. Mater. 8, 12 pp, 2013.
International Search Report and Written Opinion for PCT/BR2019/050399, dated Dec. 17, 2019.
Demand and Article 34 Amendments for PCT/BR2019/050399, Jul. 13, 2020.
Response to Written Opinion for PCT/BR2019/050399, dated Jul. 7, 2020.
Written Opinion for PCT/BR2019/050399, dated Oct. 16, 2020.

\* cited by examiner

DENTAL AND MEDICAL COMPOSITIONS HAVING A MULTIPLE SOURCE OF METALLIC IONS

FIELD OF THE INVENTION

The present invention is in the field of medicine and dentistry.

BACKGROUND

Caries is a process caused by bacteria that leads to the destruction of dental tissues and can lead to loss of the dental element if not treated in time. Once installed, its evolution can be divided into 3 phases. In the first phase caries reaches only tooth enamel; in a second phase, it deepens and invades the dentin; in the third phase it reaches the root canal. In the second and mostly in the third phase, toothache is caused mainly by the inflammatory process caused by bacterial aggression.

In order to prevent the carious process and return normal tooth function, various techniques and procedures, using different materials, are used in the treatment of caries. After caries diagnosis, the first step is the total or partial removal of the carious tissue followed by the steps for protecting the pulp (arteries, veins and nerves) and definitive restoration of the tooth. Two materials are used for tooth restoration. A first material, named intermediate restorative material, is used internally and has biological properties that protects the pulp, and a second material, called definitive restorative material, is used externally and restores the external shape of the tooth. The protection of the pulp with intermediate restorative material prior to the final restorative material is necessary since the final restorative materials, besides not having biological properties to protect the pulp, are usually aggressive to the pulp. It is desirable that these intermediate materials have the ability to create an inhospitable environment for bacterial growth by means of a high pH in addition to having a bioactivity ability to promote the repair of pulp and the remaining dentin.

Among products commonly used as final restorative materials or as root canal filling materials are calcium hydroxide and glass ionomers cements, but in recent years, with the advancement of bioactivity evaluation methods, it is known that the effectiveness of these materials in the treatments is affected by their properties. Some studies have demonstrated that the effect of bioactivity on the use of calcium hydroxide or glass ionomer-based cements, for example, in a carious lesion is extremely low, being equivalent to inert materials such as wax (Corralo D J, Maltz M (2013) "Clinical and ultrastructural effects of different liners/restorative materials on deep carious dentin: A randomized clinical trial." Caries Research 47, 243-50), for indirect pulp capping treatments in primary or permanent teeth (Marchi J J, de Araujo F B, Froner A M, Straffon L H, Nor J E (2006) "Indirect pulp capping in the primary dentition: a 4-year follow-up study" Journal of Clinical and Pediatric Dentistry 31, 68-71; Baratieri L N, Machado A, Van Noort R, Ritter A V, Baratieri N M M (2002) "Effect of pulp protection technique on the clinical performance of amalgam restorations: three-year results" Operative Dentistry 27, 319-24).

Bioceramics can be classified as bioinert, bioactive or bio-resorbable materials, based on their surface chemical reactivity (Heness G, Ben-Nissan B (2004). Innovative bioceramics. Materials Forum, 27, 104-14; 10). Bioactive materials are materials capable of forming a chemical bond with living tissues. In the context of bone replacement materials, the bioactivity of a material is commonly characterized by its ability to induce the formation of an apatite layer on its surface after immersion in biological fluids (Hench L L, Splinter R J, Allen W, Greenlee T (2004) "Bonding mechanisms at the interface of ceramic prosthetic materials." Journal of Biomedical Materials Research, 5, 117-141).

After a preliminary definition of biomaterial in the 1950s, based mostly on the criterion of maximum biochemical and biological inertia when in contact with body fluids (first generation of implantable materials), the discovery of Bioactive Glass by Larry L. Hench in 1969 was the first inorganic material to present bioactivity and an alternative to the materials used at the time in implants.

One of the main bioactivity characteristics of these Bioactive Glasses was based on the activity of Ca and Si ions present in their composition, capable of inducing the formation of a layer of carbonated hydroxyapatite on its surface similar to the mineral phase of bone (Baino F, Hamzehlou S, Kargozar S (2018) "Bioactive Glasses: Where Are We and Where Are We Going?" Journal of Functional Biomaterials 9, 25).

The second generation of Bioactive Glasses was capable of promoting a positive response of the living system through the formation of a strong and stable tissue-implant bond with the tissues where they were implanted, extending the concept of biocompatibility (Fiume E, Barberi J, Verné E, Baino F (2018) "Bioactive Glasses: From Parent 45S5 Composition to Scaffold-Assisted Tissue-Healing Therapies." Journal of Functional Biomaterials 9, 24).

In the 80's, it was discovered that Bioactive Glasses when used in the form of particles were able to promote regeneration and stimulate osteogenesis, a process of bone formation. Later, it was discovered that the metal ions present in the composition and released during the dissolution of Bioactive Glasses were responsible for the stimulation of growth factors and cell differentiation (Hench L L and Jones J R (2015) "Bioactive Glasses: Frontiers and Challenges." Frontiers in Bioengineering and Biotechnology 3, 194).

Despite their high bioactivity, Bioactive Glasses have an amorphous, non-crystalline structure, with numerous physical and chemical disadvantages, including: high brittleness, low flexural strength, low tenacity, difficult handling, low cohesiveness and high solubility. One of the ways found for the use of Bioactive Glasses is in the form of scaffold which limits its clinical application (Wu C and Chang J (2013) "A review of bioactive silicate ceramics." Biomedical Materials 8, 032001).

In the late 60's, the interest in using various ceramic materials for biomedical applications arises as an alternative to Bioactive Glasses, mostly because they present low solubility and better mechanical strength. A little later, these materials were denoted Bioceramic (Dorozhkin S V (2010) "Calcium Orthophosphates as Bioceramics: State of the Art." Journal of Functional Biomaterials, 1, 22-107).

Over the last few years new dental compositions based on these new bioceramics have been proposed to replace calcium hydroxide and glass ionomer cements with the main objective of increasing bioactivity. Among these new bioceramics are the classes of cements based on calcium silicates, which are ceramics that are presented as an alternative source of calcium, available in the form of powder/liquid or in the form of non-aqueous pastes.

Studies have shown a relationship between the ion release rate and the bioceramics bioactivity. Although calcium-rich compositions may appear more attractive as they provide a faster release of Ca$^{2+}$ ions and facilitate the formation of the apatite hydroxide layer on its surface, calcium does not appear to be an essential element in the composition for the ceramics to have bioactivity. This fact is evidenced with the nanostructured forsterite that is degradable and bioactive, even being a calcium-free material (Kharaziha M, Fathi M H (2009) "Synthesis and characterization of bioactive forsterite nanopowder." Ceramics International, 35, 2449-2454). Therefore, although calcium silicate-based bioceramic compositions have the ability to release calcium ions, they do not provide other metallic ions (Mg$^{2+}$, Zr$^{4+}$, Sr$^{2+}$, Zn$^{2+}$) which are essential for a higher bioactivity and which are capable of inducing complete regeneration and repair. It has been proven that metal ions play an important role in innumerable processes related to cell repair and regeneration, besides stimulating bone formation (Mohammadi H, Hafezi M, Nezafati N, Heasarki S, Nadernezhad A, Ghazanfari S M H, Sepantafar M (2014) "Bioinorganics in Bioactive Calcium Silicate Ceramics for Bone Tissue Repair: Bioactivity and Biological Properties." Journal Ceramic and Science Technology 5, 1-12). This bioactivity process is directly correlated with the exchange rate of the metal ions at the ceramic interface with the physiological environment surrounding it and thus being able to induce the formation of a silica rich layer on the ceramic surface (Iwata N Y, Lee G H, Tokuoka Y, Kawashima N (2004) "Sintering behavior and apatite formation of diopside prepared by coprecipitation process." Colloids and Surfaces B, 34, 239-245).

In dentistry, regeneration is defined as the formation of a physiological dentin, whereas repair is the formation of a new tissue resembling the native pulp-dentin complex at the histological level with the expected physiological functions (Smith A J, Duncan H F, Diogenes A, Simon S, Cooper P R (2016) "Exploiting the bioactive properties of the dentin-pulp complex in regenerative endodontics." Journal of Endodontics 42, 47-56). Although one of the main goals of the dental procedure is the complete regeneration of tissues lost through injury, it is unlikely that the bioceramic compositions currently available on the market are capable of stimulating tissue regeneration and repair in a significant way.

Studies have shown that metal ions, such as calcium (Ca$^{2+}$), silicon (Si$^{4+}$), strontium (Sr$^{2+}$), zinc (Zn$^{2+}$), boron (B$^{3+}$), vanadium (V$^{3+}$), cobalt (Co$^{2+}$), magnesium (Mg$^{2+}$) and zirconium (Zr$^{4+}$) are involved in bone metabolism and play a physiological role in the angiogenesis responsible for the growth and mineralization of bone tissue. The metal ions act as enzymatic cofactors and therefore influence cell signaling pathways and stimulate the effects that occur during tissue formation. These effects make metallic ions attractive for use as therapeutic agents in the engineering fields of hard and soft tissues by promoting regeneration and repair (Hoppe A, Güldal N S, Boccaccini A R (2011), "A review of the biological response to ionic dissolution products from bioactive glasses and glass-ceramics." Biomaterials 32, 2757-2774).

The first report of bioceramic cement with bioactivity properties, i.e. with the ability to release metallic ions, was performed by Torabinejad in U.S. Pat. No. 5,415,547, which proposed a Portland cement-based restorative material for dental structures, known as mineral trioxide aggregate (MTA). Although using calcium silicates, which are less soluble than calcium hydroxide, as the source of calcium ions, the product has low physico-chemical properties because it is practically Portland cement in powder form added with a radiopacifier. Although they are considered as materials having some bioactivity and although their degradation products do not induce an inflammatory reaction, the calcium silicate-based cements show numerous disadvantages related to their physical and biological properties, including: low mechanical strength, which makes them improper to load-bearing applications and low chemical stability (high rate of degradation), leading to a highly alkaline condition in the surrounding environment, which makes it detrimental to cell viability and limits their biological applications at long-term. In the literature it is possible to find numerous reports on the difficulties of using MTA mainly due to inadequate handling features.

In U.S. Patent Application No. 2003/0159618, Primus disclosed a process for making a white dental cement without the presence of iron and also based on the composition of a Portland cement. This process results in a material that can be used as dental cement for restoration. However, this process only decreased the iron content, but did not improve the physical and biological properties of these materials.

In U.S. Pat. No. 8,475,811, Yang developed a hydraulic cement formulation for dental and orthopedics applications. The focus of U.S. Pat. No. 8,475,811 was to obtain a pre-mixed paste with the presence of calcium silicates and a water-free carrier liquid, having the ability of setting with the humidity of the physiological medium. In the formulation developed by Yang, the setting mechanism occurs by hydration of the tricalcium-silicate (Ca$_3$SiO$_5$) and dicalcium-silicate (Ca$_2$SiO$_4$) phases that when in contact with the humidity of the physiological environment hydrate and form two new phases: a calcium hydroxide phase (Ca(OH)$_2$) and a silicate hydrate gel phase (3CaO$_2$SiO$_2$.3H$_2$O), known as CSH. The entanglement of this C—H—S phase together with calcium hydroxide plates from medium saturation decreases the mobility of the particles and promotes the setting of the material. The hydration reactions of tricalcium-silicate (Ca$_3$SiO$_5$) and dicalcium-silicate occur according to the following equations:

$$2Ca_3SiO_5 + 6H_2O \rightarrow 3CaO.2SiO_2.3H_2O + 3Ca(OH)_2$$

$$2Ca_2SiO_4 + 4H_2O \rightarrow 3CaO.SiO_2.3H_2O + Ca(OH)_2$$

Despite solving the handling problem of MTA (powder/liquid) through a single, injectable calcium silicate paste, Yang's ready-to-use cement did not provide additional metal ions to improve MTA bioactivity, both formulations having calcium silicates as the sole source of calcium ions.

In U.S. Pat. No. 8,765,163 B2, Zreiqat disclosed a new biocompatible material, described as being a zinc and calcium silicate. The material was developed to be used in regenerating tissues, including bone tissue. The proposed material was also described as to be used as a coating to improve the long-term stability of implantable medical devices. The material described by Zreiqat refers to Hardystonite (Ca$_2$ZnSi$_2$O$_7$) modified with Sr, Mg or Ba by sol-gel synthesis. After modification, Hardystonite is transformed into a new calcium silicate structure containing strontium, zinc and having the following formula Sr$_{0.1}$Ca$_{1.2}$ZnSi$_2$O$_7$. The disclosure of Zreigat relates specifically to materials used as implants, such as: 3D, orthopedic, dental, spine, craniofacial reconstruction, alveolar ridge augmentation and cartilage regeneration prostheses, among other implant types. Although the implantable medical device shows better bioactivity due to the presence of other metallic ions besides calcium, it was only provided in the form of devices making it impossible to be used as a restorative and/or sealing material. Therefore, in certain situations, it is not possible to use these sintered parts or implants, such as the induction of the end of root formation in vital permanent teeth with inflamed dental pulp (Apicigenesis) or in the formation of apical barrier of hard tissue in young teeth, with incompletely formed roots and necrotic pulp (Apicification).

Therefore, there is a need for the development of medical and dental compositions that have, in addition to adequate physicochemical properties of handling and setting time and the desired bioactivity allowing their use as restorative and/or root sealing material with increased biological responses (Da Rosa W L O, Cocco A R, Silva T M et al. (2018) "Current trends and future perspectives of dental pulp capping materials: a systematic review." Journal of Biomedical Materials Research. Part B, Applied Biomaterials 106, 1358-1368). Currently, considerable efforts are taken in the field of medicine and dentistry in order to obtain and develop materials having better bioactivity properties as current bioceramic compositions have not been developed considering their biological potential (Sadaghiani L, Gleeson H B, Youde S, Waddington R J, Lynch C D, Sloan A J (2016) "Growth factor liberation and DPSC response following dentine conditioning." Journal of Dental Research 95, 1298-1307).

The use of silicates of multiple metal ions in the manufacture of medical and dental implants is known in the art. Several references report the positive effect of the use of bone or dental implants containing such silicates on physiological and restorative aspects of parts or implants produced with them in the sintered form.

However, in certain situations it is not possible to use these sintered parts or implants, especially in situations in which flow of material is necessary for complete filling in the medical or dental application site of the affected area, such as endodontic filling or resorption of the root of the tooth or the opposite faces of fractured bones or even the filling of spaces between the bone or tooth with implants

SUMMARY

The present disclosure solves the structural problems of the amorphous compositions of the bioactive glasses and improves the bioactivity when compared with bioceramics described in the prior art by providing in bioceramic compositions significant differentials from the prior art, so as increased bioactivity, in situations depending on the flow of the material for complete filling.

The present disclosure provides bioceramic compositions for medical and dental uses which comprise a multiparticulate crystalline multimetallic silicate. In some embodiments, the multiparticulate crystalline multimetallic silicate is a sorosilicate. In some embodiments, the sorosilicate is Strontium-akermanite ($Sr_2MgSi_2O_7$), Akermanite ($Ca_2MgSi_2O_7$), Baghdadite ($Ca_3ZrSi_2O_9$), Hardystonite ($Ca_2ZnSi_2O_7$), or a combination thereof.

BRIEF DESCRIPTION OF THE FIGURES

FIG. 3A shows a Gilmore-type metric indenter and stainless-steel ring mold. FIG. 3B shows an indentation vertically onto the horizontal surface of the sample. FIG. 3C shows marks of indentations until they are no longer visible.

FIG. 4A shows stainless-steel ring mold filled with samples. FIG. 4B shows Petri dishes with cured samples after covered of water for 24 h. FIG. 4C shows samples after drying.

FIG. 5A shows a glass plate with the sample. FIG. 5B shows two glass plates and an additional mass. FIG. 5C shows a compressed disc of sample.

FIG. 6A shows a polypropylene ring mold filled with samples and an aluminum step wedge. FIG. 6B shows a polypropylene ring mold filled with samples and an aluminum step wedge. FIG. 6C shows a polypropylene ring mold filled with samples and an aluminum step wedge.

FIG. 7A shows two optically flats squares and a loading device. FIG. 7B shows two optically flats squares after loading. FIG. 7C shows a micrometer by determining the thickness.

DETAILED DESCRIPTION

Figure 1:
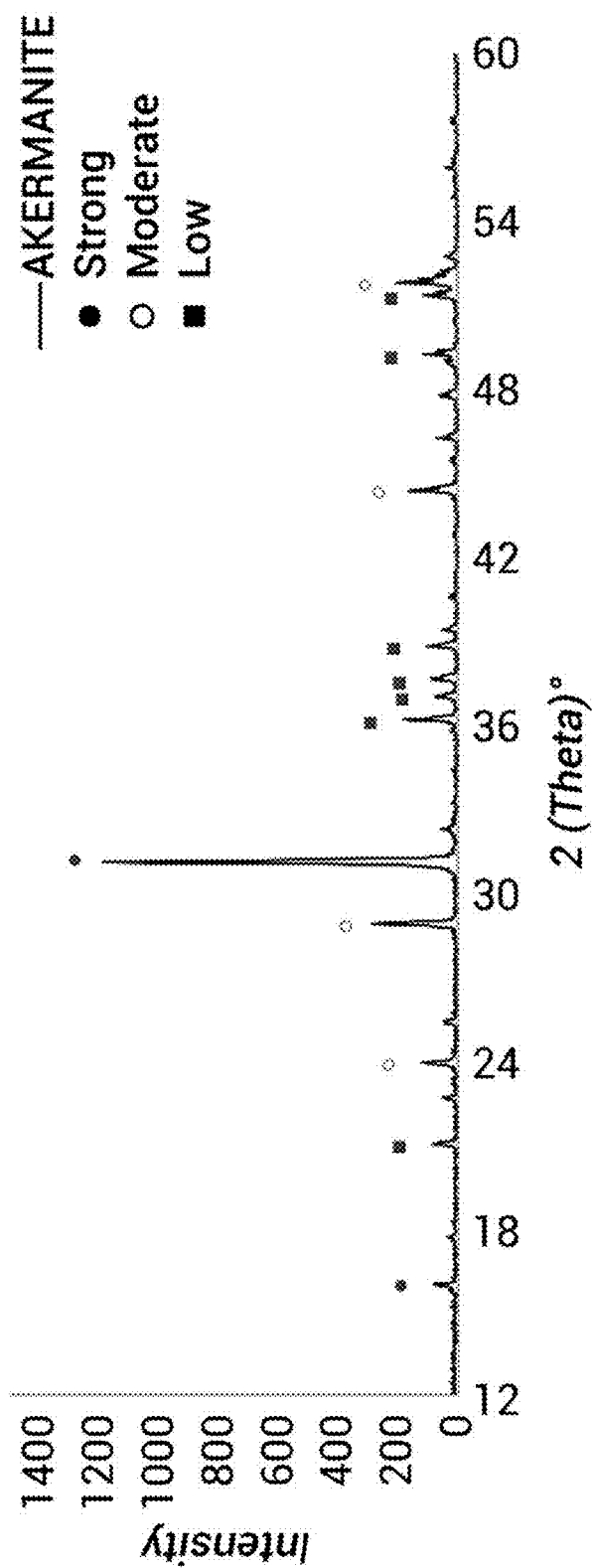
FIG. 1 is a graph describing the X-ray diffraction patterns of pure akermanite obtained via solid state reaction.

The present inventors have verified that incorporation of multiparticulate crystalline multimetallic silicates into dental or bone cement formulations is possible, but also that the dissolution rate and the pH around the application area are physiologically acceptable. They also verified that certain multiple silicates, when in the multiparticulate form, have structuring characteristics in the cavity or place of application.

This disclosure provides bioceramic compositions, in powder/liquid or paste forms, comprising multiparticulate crystalline multimetallic silicates, as a source of metallic ions, such as $Ca^{2+}$, $Mg^{2+}$, $Zr^{4+}$, $Sr^{2+}$, $Zn^{2+}$, for promoting bioactivity. The disclosed compositions can be used in medical and dental applications, for example, for use in tissue regeneration, including bone tissue. However, it will be appreciated that the compositions are not limited to these particular applications.

Crystalline multimetallic silicates are silicate materials having crystalline structure of two tetrahedron of the anionic group $(Si_2O_7)^{6-}$ linked by an oxygen ion and therefore with a negative charge of six (−6). This crystalline structure has an hourglass shape with the oxygen ion in the center being shared by the double tetrahedron, in a silicon/oxygen ratio of 2/7 and the double tetrahedron are in turn linked together by the different metal cations present in their formulation. Compounds having said structure are named sorosilicates.

The structure of the sorosilicates exhibit differences in crystalline structure and chemical composition when compared to nesosilicates, such as, tricalcium-silicate ($Ca_3SiO_5$) and dicalcium-silicate ($Ca_2SiO_4$). The nesosilicates have a crystalline structure of isolated silica tetrahedron $(SiO_4)^{4-}$ bound by a single metal ion, $Ca^{2+}$. The crystalline structure of the sorosilicates consists of two silica tetrahedra connected by a shared oxygen atom $(Si_2O_7)^{6-}$ through a covalent bond (Si—O), these double tetrahedra of silica being bound by two metallic ions selected from $Ca^{2+}$, $Mg^{2+}$, $Zr^{4+}$, $Zn^{2+}$, and $Sr^{2+}$.

Due to their crystalline structure and chemical formulation, sorosilicates have unique characteristics in terms of bioactivity. Their double tetrahedron of silica gives them a low solubility that when releasing their multiple metallic ions in a constant and balanced manner it is able to promote the osteogenic differentiation of the osteoblasts, the cells of the dental pulp, the stromal cells of the bone marrow; stem cells derived from adipose tissue, fibroblasts and periodontal ligament cells (Hoppe A, Güldal N S, Boccaccini A R (2011), "A review of the biological response to ionic dissolution products from bioactive glasses and glass-ceramics." Biomaterials 32, 2757-2774); and are also able to accelerate bone regeneration in vivo.

In addition, sorosilicates have a relatively wide range of chemical compositions and their physical, chemical and biological properties can be optimized to meet tissue regeneration requirements according to the employed metal ion type.

Examples of suitable crystalline multimetallic silicates are the compounds of the sorosilicate group, such as Strontium-akermanite ($Sr_2MgSi_2O_7$), Akermanite ($Ca_2MgSi_2O_7$), Baghdadite ($Ca_3ZrSi_2O_9$) and Hardystonite ($Ca_2ZnSi_2O_7$).

The structuring mechanism of the bioceramic compositions described herein is distinct from compositions based on calcium silicates, which when hydrated form a C—S—H phase. When the bioceramic compositions described herein are in contact with water, the calcium sulfate hemihydrate ($CaSO_4 \cdot \frac{1}{2}H_2O$) present in their composition is dissolved into dihydrate ($CaSO_4 \cdot 2H_2O$), which is poorly soluble causing a saturation in the physiological environment and, consequently, precipitation in needles-shaped crystals. The imbrication of these calcium sulfate dihydrate needles ($CaSO_4 \cdot 2H_2O$) with hydrated sorosilicate crystals ($M_1 \cdot M_2 \cdot Si_2O_7 \cdot H_2O$) imparts cohesion and mechanical strength to the bioceramic compositions described herein, at the same time as the interaction between growing crystals causes a small desirable expansion, the mechanism of the reaction can be demonstrated in the following equation, in which $M_1$ and $M_2$ are independently selected from $Ca^{2+}$, $Mg^{2+}$, $Zr^{4+}$, $Sr^{2+}$, and $Zn^{2+}$:

$$M_1M_2Si_2O_7 + (CaSO_4 \cdot \tfrac{1}{2}H_2O) + H_2O \rightarrow M_1 \cdot M_2 \cdot Si_2O_7 \cdot H_2O + CaSO_4 \cdot 2H_2O + heat$$

The bioceramic compositions disclosed herein, when contacted with the body fluid, release the metal ions ($M^+ = Ca^{2+}$, $Mg^{2+}$, $Zr^{4+}$, $Sr^{2+}$, or $Zn^{2+}$) which are exchanged for $H^+$ by the breakage of the silicon-oxygen-metal (Si—O-$M^+$) bond. Then, these $H^+$ ions bind to the silicate $(Si_2O_7)^{6-}$ to form a silica-rich amorphous colloidal layer (Si—OH) known as silanol, the reaction is demonstrated in the equation below:

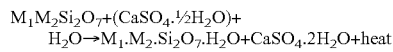

$$Si{-}O{-}M^+ + H^+ + OH^- \rightarrow Si{-}OH + M^+(aq) + OH^-$$

After formation of the silanol groups, the pH of the solution increases at the surface of the material causing condensation and re-polymerization thereof to form a layer of silica gel on the surface of the bioceramic composition, according to the reaction described in following equation:

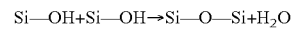

$$Si{-}OH + Si{-}OH \rightarrow Si{-}O{-}Si + H_2O$$

As a result of these initial steps, the surface of the bioceramic compositions disclosed herein exhibit an alkaline pH and an adequate concentration of multiple metal ions, in which this constant release of the metal ions in a chemically balanced environment allows for enzymatic changes that will influence and stimulate cellular differentiation and, thus, tissue formation promoting repair and regeneration of the affected area, more specifically, repair and regeneration of tissue-bone and dentin-pulp complexes.

In an embodiment, the bioceramic compositions are available in the form of powder phase and an aqueous liquid carrier.

In an embodiment, the bioceramic compositions are available in the form of non-aqueous pastes.

In a further aspect, the bioceramic compositions show radiopacity, that is, the ability of the material to reflect the X-rays used in a radiological examination. This feature is very important for material used within the dental and medical field. To impart this feature to the material, various radiopacifying agents can be used for both, the powder and paste forms, for example derivatives of barium, zirconium, bismuth, tantalum, titanium, tungsten, among others, but not limited thereto. Examples of suitable radiopacifying agents are barium sulfate, zirconium oxide, bismuth oxide, tantalum oxide, titanium oxide, and calcium tungstate. In an embodiment, the radio-opacifying agent is calcium tungstate.

In a further aspect, the bioceramic compositions comprise a setting agent. To impart this hardening to the composition, various setting agents can be used for both, powder and paste forms, such as calcium acetate, calcium sulfate, calcium carbonate, calcium oxalate, potassium sulfate, or a combination thereof. In an embodiment, suitable setting agents are calcium sulfate and potassium sulfate.

In some embodiments, water is used as a carrier of the liquid phase of the composition.

In a further aspect, the bioceramic compositions comprise an accelerator agent. To impart this feature to the material, various accelerator agents may be used in the aqueous liquid carrier comprising at least one selected from calcium chloride, calcium nitrate, calcium formate, calcium gluconate, calcium lactate, citric acid, or a combination thereof. A suitable plasticizer of the composition may be used in the liquid phase, such as, for example, at least one of materials derived from polyvinyl pyrrolidone, polyvinyl alcohol, polyethylene glycol, or combinations thereof.

Suitable non-aqueous liquid carriers of the compositions in the form of a non-aqueous paste can be members of a glycol group, such as ethylene glycol, propylene glycol, polyethylene glycol, polypropylene glycol, glycerin, diethylene glycol dimethyl ether, diethylene glycol monoethyl ether, butylene glycol, or combinations thereof.

The bioceramic compositions disclosed herein can also comprise a rheology control agent incorporated into the paste for rheology adjustment. Suitable rheology control agents can be selected from micro and nano-sized inorganic particles of different silicon oxides group, such as hydrophilic pyrogenic silica, silicon oxide, fumed silica or combinations thereof.

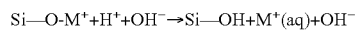

In an embodiment, the bioceramic compositions have a powder phase and an aqueous liquid carrier, wherein the solid phase comprises from 20 to 90% by weight of at least one multiparticulate crystalline multimetallic silicate, from 10 to 50% by weight of a radiopacifying agent, from 1 to 20% by weight of a setting agent, and wherein the aqueous liquid carrier comprises from 50 to 98% by weight of a vehicle, from 2 to 30% by weight of an accelerator agent and from 0.5 to 10% by weight of a plasticizer. In an embodiment, the solid phase comprises from 40 to 70% by weight of at least one multiparticulate crystalline multimetallic silicate, from 20 to 40% by weight of a radiopacifying agent, from 2 to 10% by weight of a setting agent, and the aqueous liquid carrier comprises from 70 to 85% by weight of a vehicle, from 5 to 20% by weight of an accelerator agent, from 1 to 5% by weight of a plasticizer.

In an embodiment, the bioceramic compositions in the non-aqueous paste form comprise from 10 to 60% by weight of at least one multiparticulate crystalline multimetallic silicate, from 30 to 70% by weight of a radiopacifying agent, from 1 to 20% by weight of a setting agent, from 0.5 to 10% by weight of a rheology control agent and from 20 to 60% by weight of a non-aqueous liquid carrier. In an embodiment, the bioceramic compositions comprise from 20 to 40% by weight of at least one multiparticulate crystalline multimetallic silicate, from 20 to 40% by weight of a radiopacifying agent, from 2 to 10% by weight of a setting agent 1 to 5% by weight of a rheology control agent and from 20 to 40% by weight of a non-aqueous liquid carrier.

This disclosure also includes the use of the disclosed bioceramic compositions for dental and medical applications, for example, for use in tissue regeneration, including bone tissue.

EXAMPLES

Example 1: Preparation of the Bioceramic Compositions in the Powder/Liquid Form

In the Bioceramic compositions 1 and 2 as described in Table 1, the solid components were firstly prepared in powder form using a planetary mixer in the following sequence: sorosilicate, radiopacifying agent and setting agent at speed below 400 rpm, about 30 minutes until complete homogenization. The aqueous liquid carrier was prepared using a mechanical stirrer and the components were added in the following sequence: water, accelerator agent and plasticizer at speed below 800 rpm, about 60 minutes until complete homogenization.

TABLE 1

Bioceramic compositions

| | Powder phase | | | Aqueous liquid carrier | | |
|---|---|---|---|---|---|---|
| Sample | Sorosilicate | Radiopacifier | Setting agent | Vehicle | Accelerator agent | Plasticizer |
| CB 1 | Akermanite 68% | Calcium tungstate 22% | Calcium sulfate/ potassium sulfate 10% | Water 75% | Calcium chloride 20% | Polyvinyl alcohol 5% |
| CB 2 | Baghdadite 68% | Calcium tungstate 22% | Calcium sulfate/ potassium sulfate 10% | Water 75% | Calcium chloride 20% | Polyvinyl alcohol 5% |

Example 2: Preparation of the Bioceramic Compositions in the Non-Aqueous Paste Form The Bioceramic compositions in Table 2, below, were prepared by mixing the liquid component (carrier) with the solid components in a mechanical stirrer, in the following sequence: sorosilicate, radiopacifier, rheology control agent and setting agent with speed below 500 rpm, approximately 45 minutes until complete homogenization.

TABLE 2

Bioceramic compositions

| | Non-aqueous Paste | | | | |
|---|---|---|---|---|---|
| Sample | Sorosilicate | Radiopacifier | Liquid carrier | Rheology control agent | Setting agent |
| CB 3 | Hardystonite 26% | Calcium tungstate 37% | Polyethylene glycol 25% | Silicon oxide 2% | Calcium sulfate/potassium sulfate 10% |
| CB 4 | Strontium- akermanite 35% | Calcium tungstate 35% | Polyethylene glycol 25% | Silicon oxide 2% | Calcium sulfate/potassium sulfate 3% |

TABLE 2-continued

Bioceramic compositions

Non-aqueous Paste

| Sample | Sorosilicate | Radiopacifier | Liquid carrier | Rheology control agent | Setting agent |
|---|---|---|---|---|---|
| CB 5 | Akermanite 22% | Zirconium oxide 35% | Polyethylene glycol 33% | Silicon oxide 2% | Calcium sulfate/potassium sulfate 8% |
| CB 6 | Akermanite 30% | Zirconium oxide 28% | Polyethylene glycol 29% | Silicon oxide 4% | Calcium sulfate/potassium sulfate 9% |

Example 3: Physico-Chemical Characterization of Bioceramic Compositions

Figure 2:
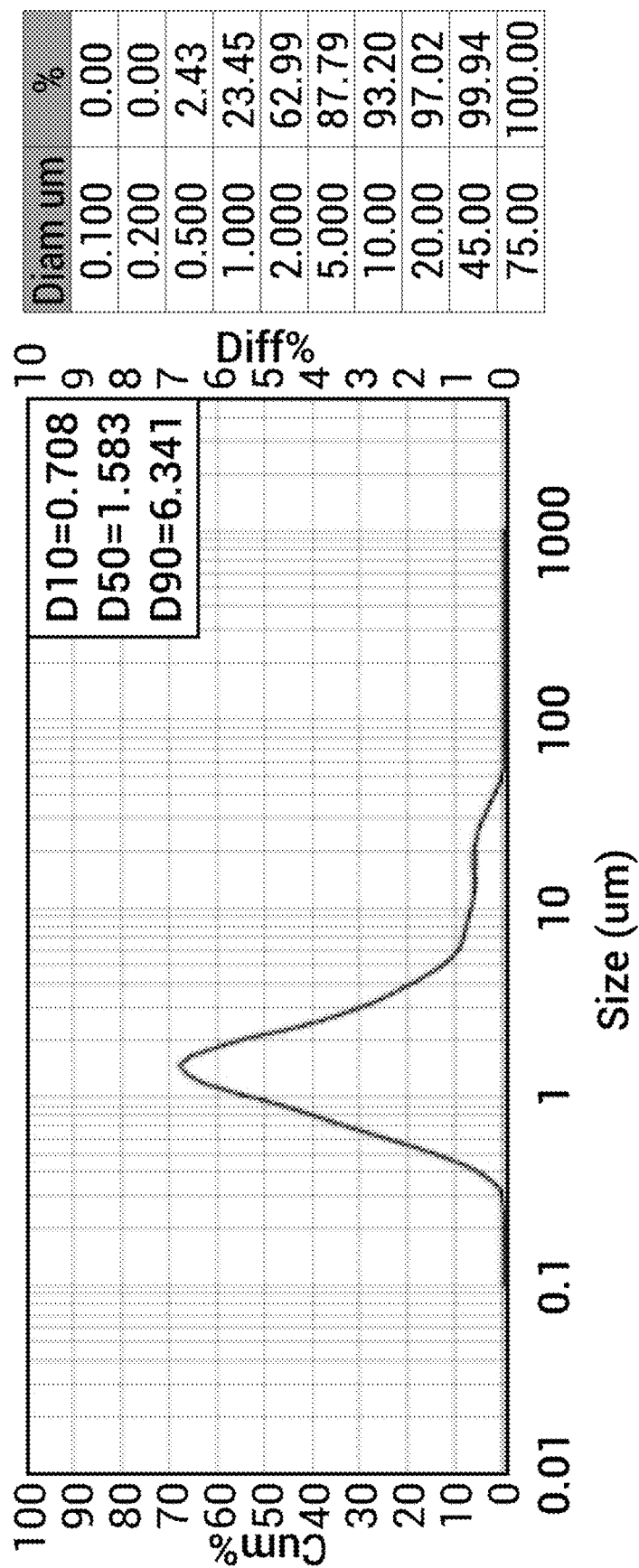
FIG. 2 is a graph describing the granulometric distribution of Baghdatite particles.

Sorosilicate component was characterized by X-ray diffraction in order to identify the constituent phases and by laser diffraction to identify their particle size distribution. FIG. 1 presents the X-ray diffraction pattern showing the characteristic peaks identification of the Akermanite sorosilicate with the presence of $Ca_2MgSi_2O_7$ crystalline phase. FIG. 2 presents the particle size distribution of the Akermanite phase with d50 less than 1.58 μm.

Figure 3A:
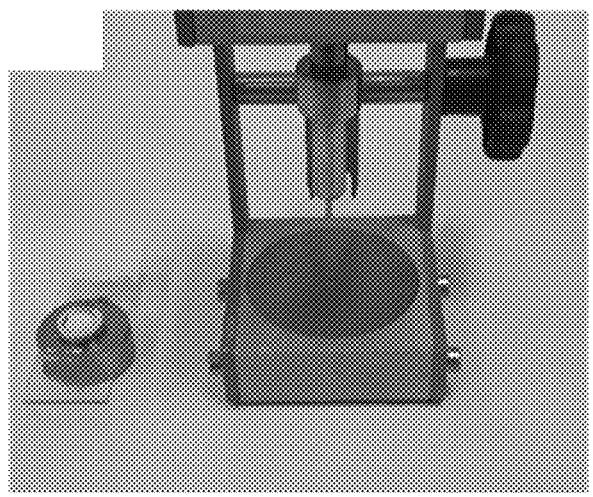
FIGS. 3A-C show the setting time assay.
Figure 3B:
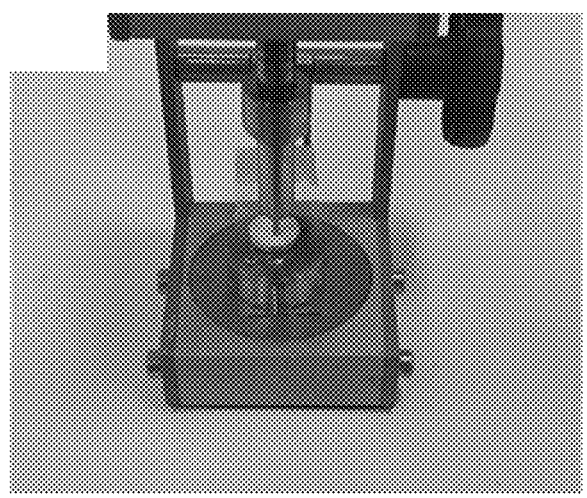
Figure 3C:
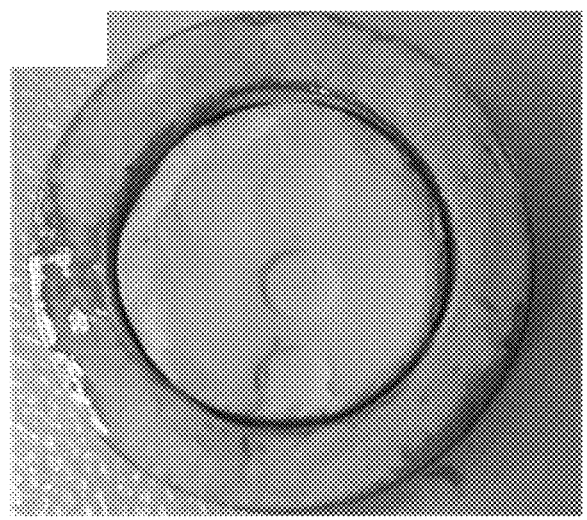

The physical-chemical characterization of bioceramic compositions 1 to 6 was performed according to ISO 6876: 2012—Dentistry—Root canal sealing materials. For the determination of the setting time, 3 specimens of each composition described in Examples 1 and 2 were produced and kept in a climatic chamber at 37±1° C. and 95±5%. Ten minutes after the samples preparation, they were subjected to marking with the aid of a Gilmore needle. The times elapsed from the beginning of the production of the samples to the moment when it was no longer possible to visualize any type of needle marking on the surface of the material were recorded (FIGS. 3A-C). The result of the setting time is shown in Table 3.

Figure 4A:
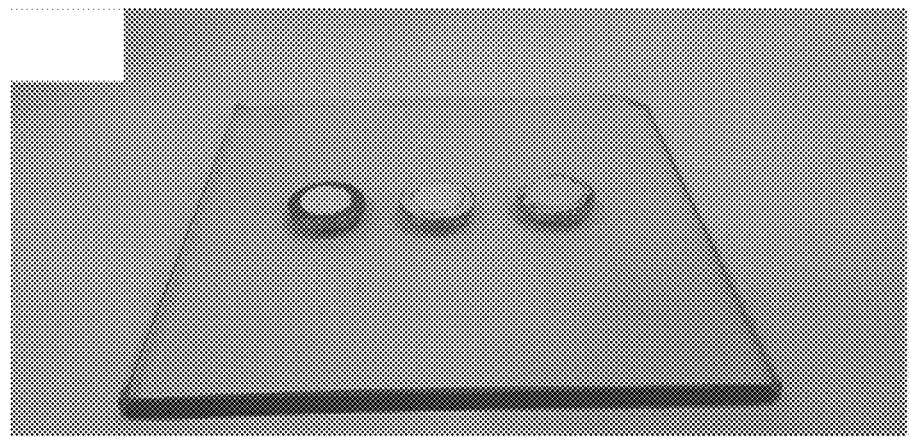
FIGS. 4A-C show the solubility test.
Figure 4B:
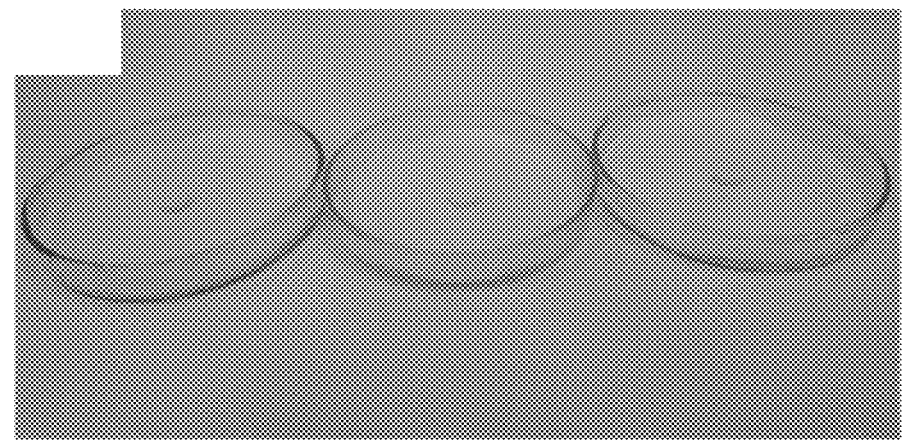
Figure 4C:
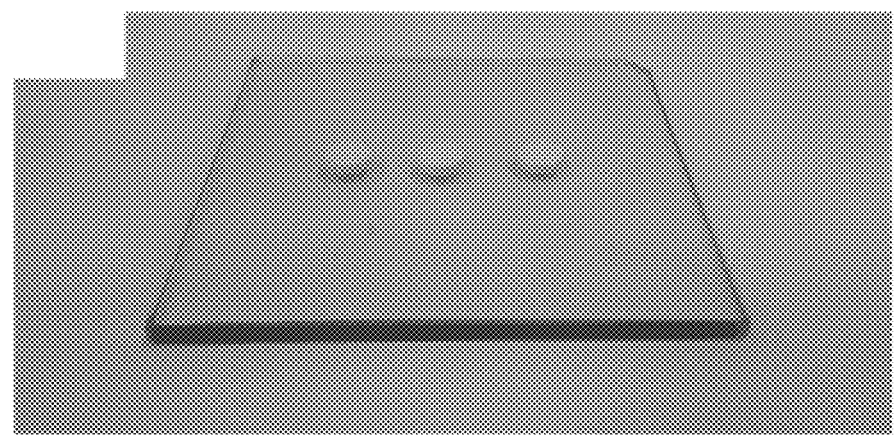

For the solubility tests two specimens with 20 mm diameter and 1.5 mm height of each composition described in Examples 01 and 02 were prepared. These samples were kept in distilled water in Petri dishes at 37° C. for 24 hours. After this period, the water accompanied by the samples was filtered on filter paper and collected on a second Petri dish (initial mass). This plate was kept in a heating muffle at 100° C. and the water was completely evaporated. Solubility was determined by the difference between the initial mass and the final mass of the Petri dish (FIGS. 4A-C) and the result is presented in Table 3.

Figure 5A:
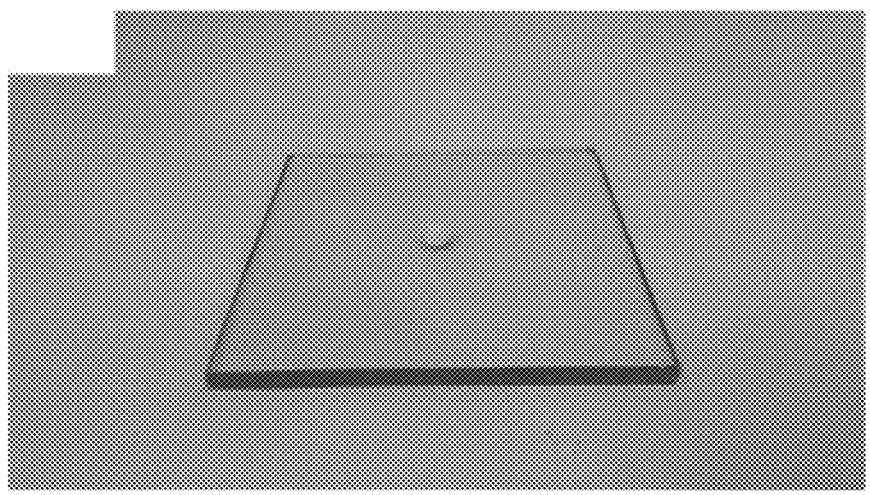
FIGS. 5A-C show the flow test.
Figure 5B:
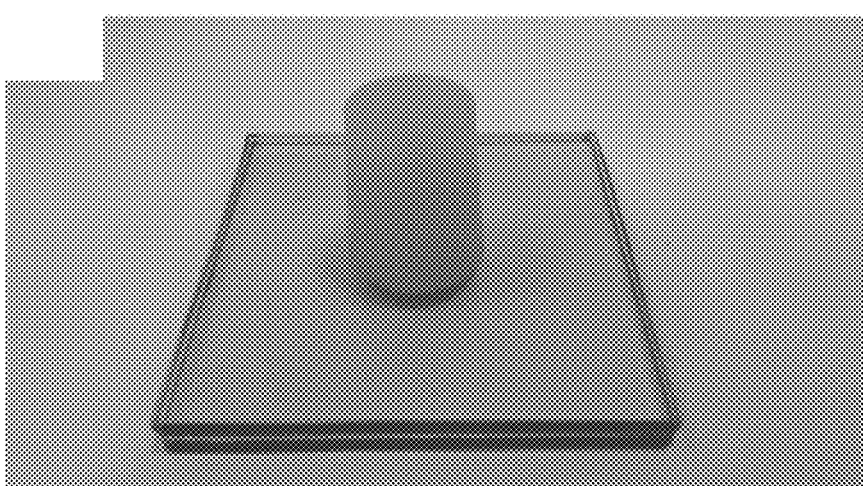
Figure 5C:
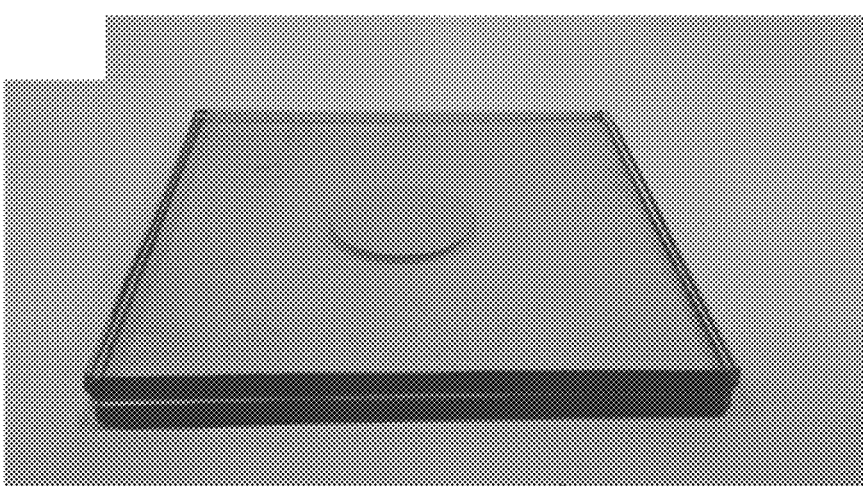

The flow was determined using three samples of each of the bioceramic compositions from 1 to 4 described on Examples 1 and 2. Two glass plates having dimensions of 40 mm (height)×40 mm (width)×5 mm (thickness) were used. With the aid of a graduated syringe, 0.050±0.005 ml of each sample was placed on one of the glass plates. After 180 seconds from the start of the sample preparation, the other glass plate, and a weight of 100 g, were placed over the material. Ten minutes after the start of the test, the weight was removed, and the largest and smallest diameters of the disk formed by the bioceramic compositions were measured (FIGS. 5A-C). The result of the flow is shown in Table 3.

Figure 6A:
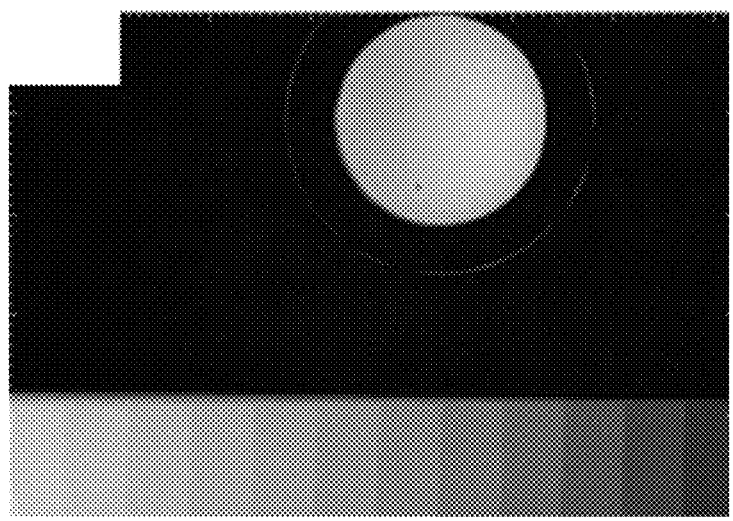
FIGS. 6A-C show the radiopacity test.
Figure 6B:
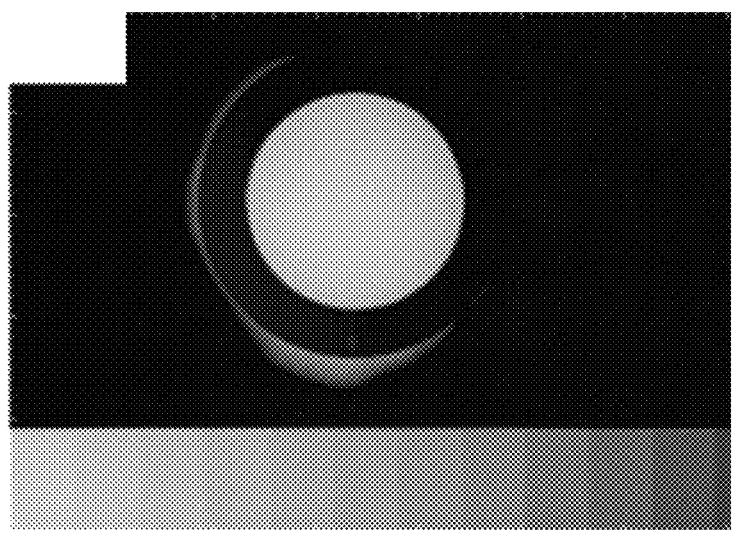
Figure 6C:
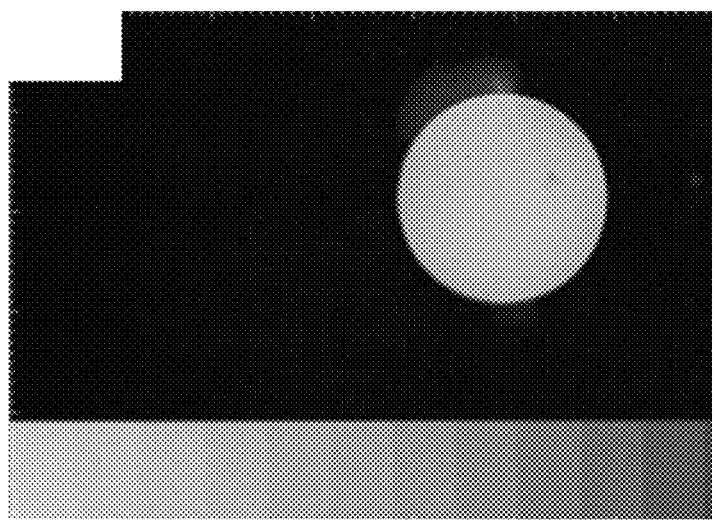

For determining the radiopacity of the bioceramic compositions 1 to 6 of Examples 1 and 2, specimens with 10 mm diameter and 1.00±0.01 mm height were produced. The samples were positioned close to an aluminum scale (1-7 mm Al) for comparison of the optical density. A digital sensor along with an X-ray emitter were used to capture the images (FIGS. 6A-C). The result of the radiopacity is shown in Table 3.

Figure 7A:
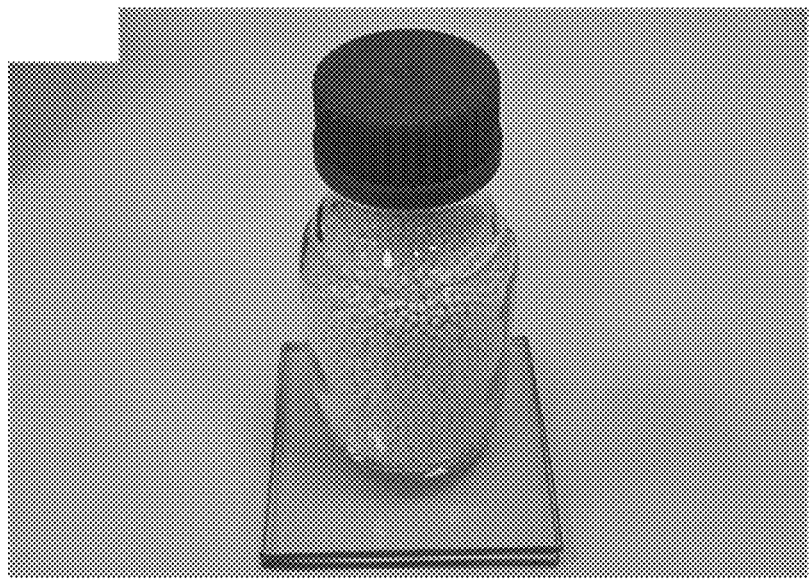
FIGS. 7A-C show the test for determining the film thickness of the compositions of the present disclosure.
Figure 7B:
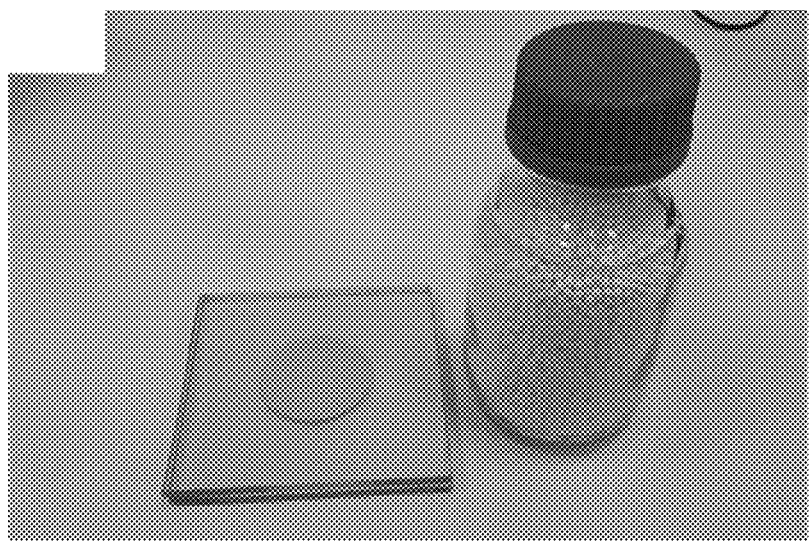
Figure 7C:
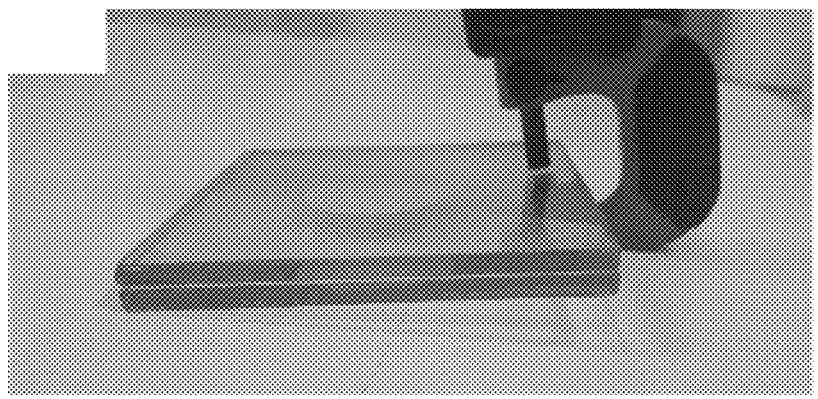

The film thickness of the bioceramic compositions 1 to 4 of Examples 1 and 2 was determined by applying the material between two flat square glass plates having a thickness of 5 mm and a contact surface of approximately 200 mm2. After 3 minutes from the application of the material, a load of 150N was applied over the set and the film thickness was measured with a micrometer (FIGS. 7A-C). This assay was repeated three times for each of the compositions and the film thickness result is shown in Table 3.

TABLE 3

Physical properties of the bioceramic compositions 1 to 6.

| | Setting time (min) | Solubility (%) | Flow (mm) | Radiopacity (mm Al) | Film thickness (μm) |
|---|---|---|---|---|---|
| CB 1 | 60 ± 17 | 1.52 ± 0.02 | 18.52 ± 2.95 | ≥6 | 27 ± 3 |
| CB 2 | 70 ± 15 | 1.64 ± 0.06 | 19.12 ± 1.17 | ≥6 | 22 ± 3 |
| CB 3 | 180 ± 20 | 2.75 ± 0.02 | 23.05 ± 2.15 | ≥6 | 14 ± 1 |
| CB 4 | 160 ± 17 | 2.64 ± 0.03 | 22.73 ± 1.75 | ≥6 | 11 ± 2 |
| CB 5 | 200 ± 35 | 1.29 ± 0.37 | 22.32 ± 1.94 | ≥6 | 37 ± 8 |
| CB 6 | 90 ± 29 | 1.02 ± 0.15 | Not applicable | ≥6 | Not applicable |

The ions release from the bioceramic compositions 1 to 6 was determined by Inductively Coupled Plasma Atomic Emission Spectroscopy (ICP-AES). Samples were prepared according to the procedure described in Examples 1 and 2. Disks of the prepared samples were kept in 30 mL of a simulated body fluid solution (SBF) pH 7.25 at 37° C. and evaluated in 1, 3, 5, 7, 10 and 20 days. The concentrations of ions from the SBF were similar to those found in human blood plasma according to Kokubo (Kokubo T (1990) "Surface chemistry of bioactive glass-ceramics" Journal of Non-Crystalline Solids 120, 138-151). Aliquots of the solution were collected at 1, 3, 5, 10 and 20 days, and the concentrations of ions ($Ca^{2+}$, $Mg^{2+}$, $Zr^{4+}$, $Zn^{2+}$, $Si^{4+}$) in the solutions were determined by ICP-AES as shown in Table 4. The pH variations of the resulting solutions were also determined with a digital pH meter. The results are presented in Table 4.

TABLE 4

Concentration of the ions released from the bioceramic compositions 1 to 6.

| | Ionic concentration (ppm) | | | | | | pH | | | | | |
|---|---|---|---|---|---|---|---|---|---|---|---|---|
| Days | CB 1 | CB 2 | CB 3 | CB 4 | CB 5 | CB6 | CB 1 | CB 2 | CB 3 | CB 4 | CB 5 | CB6 |
| 1 | Ca(180) Mg(50) Si(52) | Ca(120) Zr(32) Si(45) | Ca(110) Zn(20) Si(40) | Sr(150) Mg(80) Si(35) | Ca(132) Mg(56) Si(23) | Ca(174) Mg(92) Si(63) | 7.7 | 8.2 | 7.5 | 9.2 | 10.2 | 10.4 |
| 3 | Ca(215) Mg(51) Si(56) | Ca(132) Zr(36) Si(47) | Ca(109) Zn(25) Si(42) | Sr(180) Mg(82) Si(32) | Ca(145) Mg(63) Si(35) | Ca(176) Mg(89) Si(58) | 8.2 | 9.0 | 8.0 | 9.4 | 11.2 | 11.6 |
| 5 | Ca(220) Mg(50) Si(54) | Ca(125) Zr(30) Si(42) | Ca(100) Zn(27) Si(37) | Sr(150) Mg(82) Si(32) | Ca(151) Mg(52) Si(35) | Ca(172) Mg(87) Si(54) | 8.0 | 9.5 | 7.6 | 9.2 | 10.2 | 10.9 |
| 10 | Ca(200) Mg(47) Si(43) | Ca(90) Zr(28) Si(39) | Ca(95) Zn(21) Si(40) | Sr(145) Mg(80) Si(38) | Ca(140) Mg(50) Si(26) | Ca(168) Mg(86) Si(51) | 8.5 | 8.7 | 7.8 | 9.0 | 10.6 | 10.8 |
| 20 | Ca(172) Mg(42) Si(38) | Ca(95) Zr(27) Si(32) | Ca(92) Zn(17) Si(39) | Sr(110) Mg(72) Si(27) | Ca(137) Mg(43) Si(19) | Ca(165) Mg(82) Si(43) | 8.7 | 8.2 | 7.4 | 9.5 | 10.4 | 10.9 |

Example 4: Assay for Determining Hydroxyapatite Formation

To evaluate the ability of hydroxyapatite formation by the bioceramic compositions, samples with a mean particle size of 1.5 μm were stored in a solution of simulated body fluid (SBF) pH 7.25 at 37° C. and evaluated at 1, 3, 5, 7, 10 and 20 days using the mass/volume ratio of 1.5 mg/mL. After 20 days the disks were washed with water and dried at 60° C. The amount of hydroxyapatite was determined by the phosphorus (P) content in the samples by dispersive energy X-ray fluorescence spectrometry. The mass percentage found is related to hydroxyapatite formation. The results are presented in Table 5.

TABLE 5

Percentages by weight of phosphorus obtained by area mapping by X-ray fluorescence of the bioceramic compositions 1 to 6.

| | Days Element P (%) | | | | | |
|---|---|---|---|---|---|---|
| Samples | 1 | 2 | 3 | 5 | 10 | 20 |
| CB 1 | 0.081 | 0.075 | 0.080 | 0.131 | 0.203 | 0.213 |
| CB 2 | 0.062 | 0.071 | 0.075 | 0.082 | 0.101 | 0.123 |
| CB 3 | 0.055 | 0.051 | 0.063 | 0.079 | 0.088 | 0.095 |
| CB 4 | 0.079 | 0.085 | 0.094 | 0.099 | 0.125 | 0.182 |
| CB 5 | 0.082 | 0.090 | 0.105 | 0.122 | 0.143 | 0.196 |
| CB 6 | 0.095 | 0.105 | 0.132 | 0.160 | 0.184 | 0.208 |

While some embodiments are shown and described herein, one skilled in the art will appreciate that modifications and variations are possible in light of the above teachings.

Example 6: Cell Viability in Human Stem Cells (hDPSCs Pulp)

The number of viable cells or cells viability after exposure to bioceramic compositions was determined using the chromogenic indicator 3-(4,5-dimethyl-thiazol)-2,5-diphenyl-tetrazolium bromide (MTT) assays for 72 hours.

The cell viability observed after incubation found was compared with control (without cements) and with a Market resin sealer (CC1), in which control showed the highest cell viability while CC1 showed the lowest, i.e., showing an unsatisfactory result for CC1.

Figure 8:
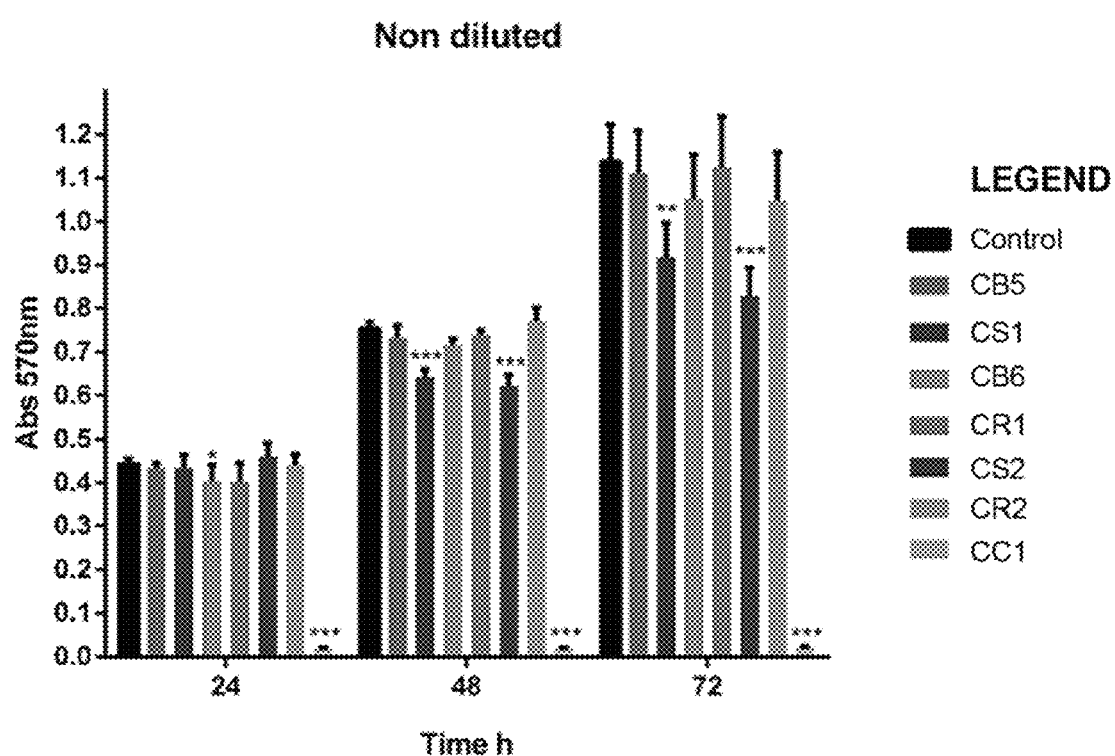
FIG. 8 shows the cell viability determined using the (MTT) assays. Asterisks represent significant differences compared with the control group (*$p<0.05$; ** $p<0.01$, $p<0.001$), wherein CB5 is Bioceramic composition sealer, CS1 is Market bioceramic sealer, CB6 is Bioceramic composition repair, CR1 is Market bioceramic repair, CS2 is Market bioceramic sealer, CR2 is Market bioceramic repair and CC1 is Market resin sealer. The order in each set of bars is, from left to right: control, CB5, CS1, CB6, CR1, CS2, CR2, and CC1.

It was also possible to see differences between Bioceramic composition sealer (CB5), Market bioceramic sealer (CS1), Bioceramic composition repair (CB6), Market bioceramic repair (CR1), Market bioceramic sealer (CS2) and Market bioceramic repair (CR2). The results are presented in FIG. 8.

Example 7: Cell Migration in Human Stem Cells (hDPSCs Pulp)

The gradual decrease in cell migration over time indicates faster healing of the damaged region and a positive response in terms of cure rate. The migration of human stem cells (hDPSCs Pulp) in the presence of bioceramic compositions, so as in the presence of a control and of a Market resin sealer, was evaluated by in vitro scratch wound-healing assay.

Figure 9:
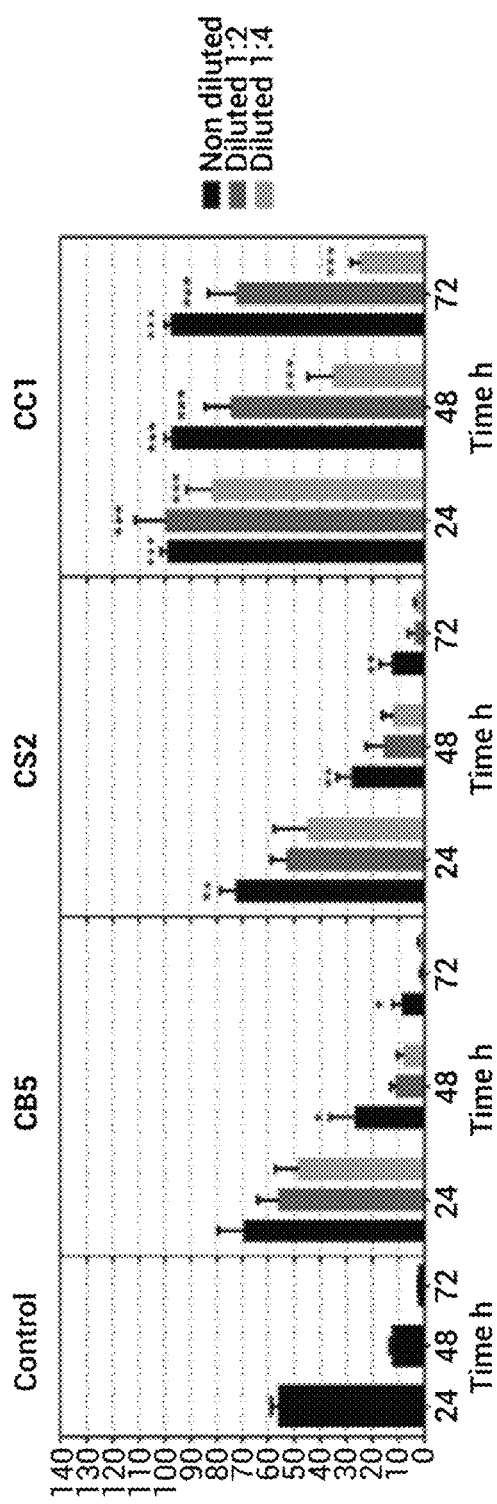
FIGS. 9 and 10 shows the migration of human stem cells (hDPSCs Pulp) exposed to extracts of different cements evaluated by in vitro scratch wound-healing assay. In which, CB5 is Bioceramic composition sealer, CS1 is Market bioceramic sealer, CB6 is Bioceramic composition repair, CR1 is Market bioceramic repair CS2 is Market bioceramic sealer, CR2 is Market bioceramic repair and CC1 is Market resin sealer.
Figure 10:
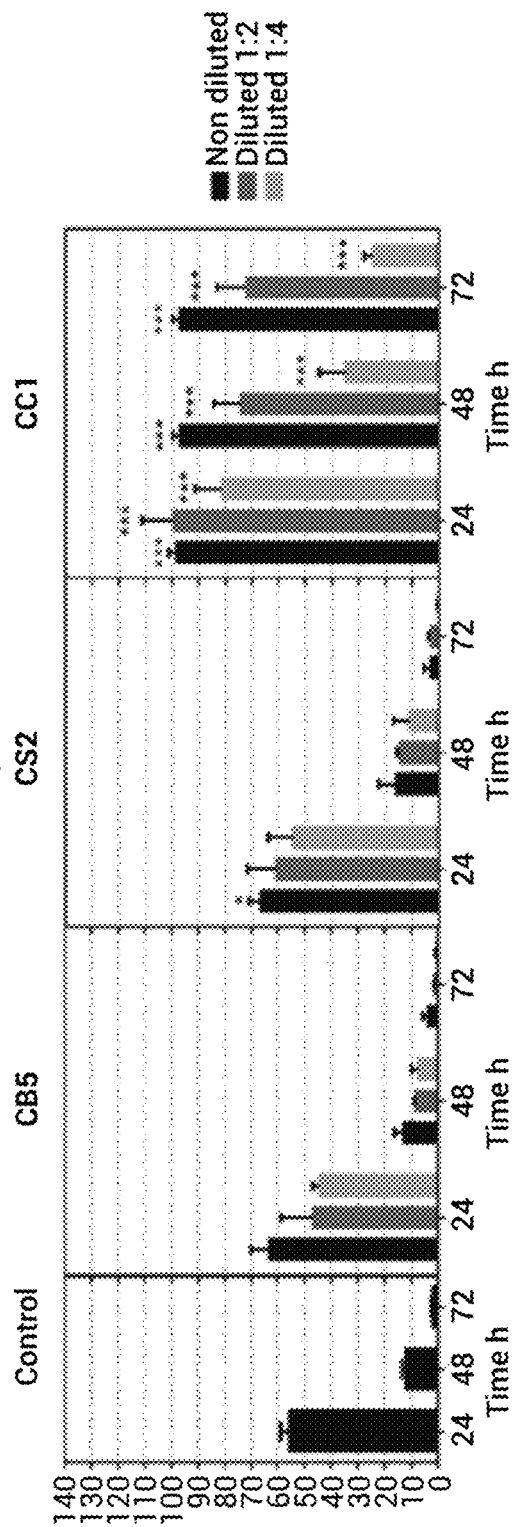
Figure 11:
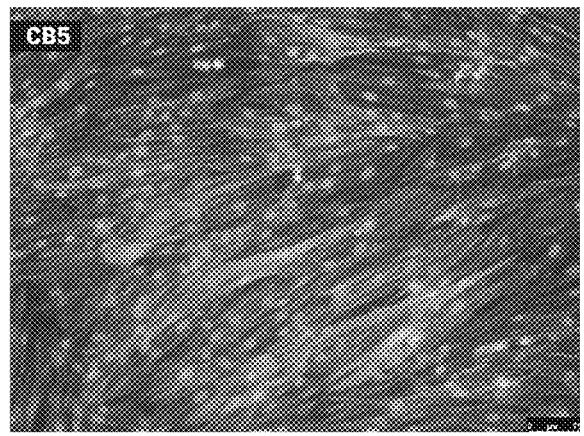
FIGS. 11 and 12, respectively, shows cell adhesion in human stem cells (hDPSCs Pulp) exposed to extracts of Bioceramic composition sealer (CB5) and Bioceramic composition repair (CB6) and, then, evaluated by in vitro scratch wound-healing assay.
Figure 12:
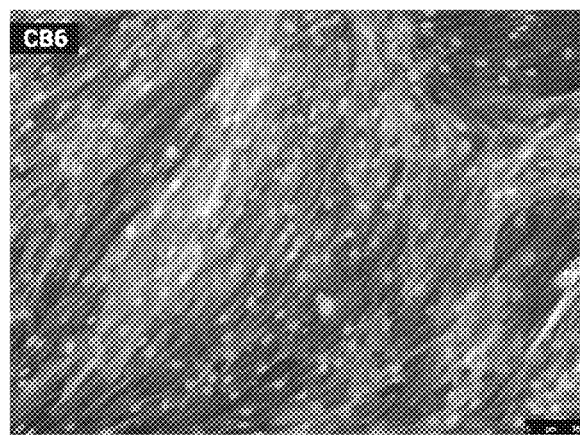

It was also possible to see differences between Bioceramic composition sealer (CB5), Market bioceramic sealer (CS1), Bioceramic composition repair (CB6), Market bioceramic repair (CR1), Market bioceramic sealer (CS2) and Market bioceramic repair (CR2), wherein the Bioceramic composition sealer (CB5) and the Bioceramic composition repair (CB6) showed lower cell migration when compared to the marked bioceramic sealer (CS1) and repair (CR2). The results are presented in FIGS. 9 and 10.

Example 8: Cell Adhesion in Human Stem Cells (hDPSCs Pulp)

Cell adhesion was also evaluated by means of in vitro scratch wound-healing assay. HDPSCs cells were analyzed by difference in staining with phalloidin (cell nucleus) and DAPI to visualize actin cytoskeleton.

Cell adhesion results showed excellent interaction and adhesion between neighboring cells in the presence of bioceramic composition. The Bioceramic composition sealer (CB5) and Bioceramic composition repair (CB6), showed a gradual increase in growth over time, an extended morphology and a high content of F-Actin (cell microfilamen), reaching confluence after 72 hours of culture.

The analysis of cell proliferation (via cell viability study), apoptosis, cell adhesion and morphology (via cell adhesion study) and migration (via cell migration study) showed very positive results, indicating that the proposed bioceramic composition induces the odonto/osteogenic mineralization and differentiation process in the presence of tooth-specific human stem cells (hDPSCs pulp). While a market resin sealer was also used in the comparative studies, however, all results were not satisfactory for this product.

The invention claimed is:

1. A bioceramic composition formulated for endodonic application comprising at least one multiparticulate crystalline multimetallic silicate, which is a sorosilicate, at least one liquid carrier and calcium sulfate as a setting agent, wherein upon hydration at a time of the endodontic application, the bioceramic composition flows and the calcium sulfate forms calcium sulfate dihydrate needles and imbricates with sorocilicate crystals, wherein the bioceramic composition hardens.

2. The bioceramic composition according to claim 1, wherein the sorosilicate is selected from the group consisting of Strontium-akermanite ($Sr_2MgSi_2O_7$), Akermanite ($Ca_2MgSi_2O_7$), Baghdadite ($Ca_3ZrSi_2O_9$), Hardystonite ($Ca_2ZnSi_2O_7$), and a combination thereof.

3. The bioceramic composition according to claim 1, which is in the form of a powder phase and an aqueous liquid carrier.

4. The bioceramic composition according to claim 3, wherein:
  (a) the powder phase of the composition comprises:
    optionally, at least one further setting agent selected from the group consisting of calcium acetate, calcium carbonate, calcium oxalate, potassium sulfate, and a combination thereof; and
    at least one a radiopacifying agent selected from the group consisting of barium sulfate, zirconium oxide, bismuth oxide, tantalum oxide, titanium oxide, and calcium tungstate, and a combination thereof; and
  (b) the aqueous liquid carrier of the composition comprises:
    water;
    at least one accelerator agent from the group consisting of calcium chloride, calcium nitrate, calcium gluconate, calcium lactate, calcium formate, citric acid, potassium sulfate, and a combination thereof; and
    at least one plasticizer from the group consisting of polyvinylpyrrolidone, polyvinyl alcohol, polyethylene glycol, and a combination thereof.

5. The bioceramic composition according to claim 4, wherein:
  (a) the powder phase of the composition comprises:
    from 40 to 70% by weight of at least one sorosilicate;
    from about 2% to about 10% by weight of at least one setting agent; and
    from about 20% to about 40% by weight of at least one a radiopacifying agent; and
  (b) the aqueous liquid carrier of the composition comprises:
    from about 70% to about 85% by weight of water;
    from about 5% to about 20% by weight of at least one accelerator agent; and
    from about 1% to about 5% by weight of at least one plasticizer.

6. The bioceramic composition according to claim 1, which is in the form of non-aqueous paste.

7. The bioceramic composition according to claim 6, wherein the non-aqueous paste form comprises:
  at least one non-aqueous liquid carrier selected from the group consisting of ethylene glycol, propylene glycol, polyethylene glycol, polypropylene glycol, glycerin, diethyleneglycol dimethyl ether, diethyleneglycol monoethyl ether, butylene glycol, and a combination thereof;
  at least one a radiopacifying agent selected from the group consisting of barium sulfate, zirconium oxide, bismuth oxide, tantalum oxide, titanium oxide, and calcium tungstate, and a combination thereof;
  optionally, at least one further setting agent selected from the group consisting of calcium acetate, calcium carbonate, calcium oxalate, potassium sulfate, and a combination thereof; and
  a rheology control agent comprising at least one micro or nano-sized inorganic particles of silicon oxide.

8. The bioceramic composition according to claim 7, wherein the silicon oxide is selected from the group consisting of silicon oxide, fumed silica, hydrophilic pyrogenic silica, and a combination thereof.

9. The bioceramic composition, according to claim 7, wherein the non-aqueous paste form comprises:
  from 20 to 40% by weight of at least one sorosilicate;
  from about 20% to about 40% by weight of at least one non-aqueous liquid carrier;
  from about 20% to about 40% by weight of at least one a radiopacifying agent;
  from about 2% to about 10% by weight of a setting agent; and
  from about 1% to about 5% by weight of a rheology control agent.

10. The bioceramic composition according to claim 1, which contains at least 10% by weight of sorosilicate.

11. The bioceramic composition according to claim 1, which has a particle size distribution with d50 less than 150 microns.

12. The bioceramic composition according to claim 1, which has a particle size distribution essentially with d50 less than 5 microns.

13. A method for inducing tissue regeneration comprising placing the bioceramic composition as defined in claim 1 into the tissue to be repaired.

* * * * *